United States Patent [19]

Wright

[11] Patent Number: 5,436,321
[45] Date of Patent: Jul. 25, 1995

[54] ANTIBODIES TO THE LIPOPOLYSACCHARIDE BONDING OPSONIN SEPTIN

[75] Inventor: Samuel D. Wright, Larchmont, N.Y.

[73] Assignee: The Rockefeller University, New York, N.Y.

[21] Appl. No.: 916,160

[22] PCT Filed: Feb. 1, 1991

[86] PCT No.: PCT/US91/00696
§ 371 Date: Jul. 31, 1992
§ 102(e) Date: Jul. 31, 1992

[87] PCT Pub. No.: WO91/11464
PCT Pub. Date: Aug. 8, 1991

Related U.S. Application Data

[63] Continuation-in-part of Ser. No. 473,609, Feb. 1, 1990, abandoned.

[51] Int. Cl.$^6$ .............. C07K 16/12; C07K 16/00; C12N 15/12
[52] U.S. Cl. .............. 530/388.25; 530/388.4; 530/389.3; 530/389.5; 435/70.2
[58] Field of Search ............ 530/388.25, 389.3, 388.4, 530/389.5; 424/85.8; 435/70.2

[56] References Cited

U.S. PATENT DOCUMENTS 4,315,906 2/1982 Gelder .................... 424/1

OTHER PUBLICATIONS

Stone, R., Science, 259:1243, 26 Feb. 1993.
Rhein, R., Biotechnology Newswatch, pp. 1 and 3, Oct. 4, 1993.
Waldmann, T. A., Science, 252: 1657–1662, Jun. 1991.
Harris, W. J. et al, Tibtech, 11: 42–44, Feb. 1993.
Kirikae, et al. Microbiol. Immunol., 32 (1), pp. 33–44, (1988).
Lo et al., J. Exp. Med., 169, pp. 1779–1793 (1989).
Lo et al., J. Immunol., 143 pp. 3325–3329 (1989).
Roeder et al., Infect. and Immunity, 57, pp. 1054–1058 (1989).
Springer et al., Biochem., 13, pp. 1379–1389 (1974).
Wright, et al., J. Exp. Med., 170, pp. 1231–1241 (1989).
Wright et al., J. Immunol. 136, pp. 1759–1764 (1986).

*Primary Examiner*—David L. Lacey
*Assistant Examiner*—Susan Loring
*Attorney, Agent, or Firm*—Klauber & Jackson

[57] ABSTRACT

An antibody to septin, in which septin is an opsonin. Septin is isolated from human serum and is present at high levels in normal serum in distinction to the acute phase protein lipoprotein binding protein (LBP). Septin is an opsonin that is capable of binding to lipopolysaccharide to form a complex that is recognized by a receptor on monocytes, macrophage cells and polymorphonuclear cells, and that possesses an apparent molecular weight of about 90 kD as determined by SDS-PAGE analysis. Utilities of the antibody are provided, and testing procedures, materials in kit form, recombinant materials and procedures, and compositions are likewise set forth.

7 Claims, 3 Drawing Sheets

ANTIBODIES TO THE LIPOPOLYSACCHARIDE BONDING OPSONIN SEPTIN

This application is a continuation-in-part of application Ser. No. 07/473,609, filed Feb. 1, 1990, now abandoned.

TECHNICAL FIELD OF THE INVENTION

The present invention relates to newly discovered and isolated proteins and to methods and compositions including such proteins for preventing or treating sepsis. More particularly, the present invention relates to a molecule that binds to lipopolysaccharide (LPS) and to the CD14 monocyte differentiation antigen, and to antibodies thereto that may thereby inhibit the binding of LPS complexes by CD14-expressing cells.

BACKGROUND OF THE INVENTION

Sepsis is morbid condition induced by a toxin, the introduction or accumulation of which is most commonly caused by infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure.

Sepsis-inducing toxins have been found associated with pathogenic bacteria, viruses, plants and venoms. Among the well described bacterial toxins are the endotoxins or lipopolysaccharides(LPS) of the gram-negative bacteria. These molecules are glycolipids that are ubiquitous in the outer membrane of all gram-negative bacteria. While the chemical structure of most of the LPS molecule is complex and diverse, a common feature is the lipid A region of LPS [E. Th. Rietschel et al., in *Handbook of Endotoxins*, 1:187-214 eds., R. A. Proctor and E. Th. Rietschel, Elsevier, Amsterdam (1984)]; recognition of lipid A in biologic systems initiates many, if not all, of the pathophysiologic changes of sepsis. Because lipid A structure is highly conserved among all types of gram-negative organisms, common pathophysiologic changes characterize gram-negative sepsis.

LPS is believed to be a primary cause of death in humans during gram-negative sepsis, particularly when the symptoms include adult respiratory distress syndrome (ARDS) [van Deventer et al., *Lancet*, 1:605 (1988); ziegler et al., *J. Infect. Dis.*, 136:19-28 (1987)]. For instance, one particular cytokine, tumor necrosis factor alpha/cachectin (TNF), has recently been reported to be a primary mediator of septic shock [Beutler et al., *N. Eng. J. Med.*, 316:379 (1987)]. Intravenous injection of LPS endotoxin from bacteria into experimental animals and man produces a rapid, transient release of TNF [Beutler et al., *J. Immunol.*, 135:3972 (1985); Mathison et al., *J. Clin. Invest.* 81:1925 (1988)]. Evidence that TNF is a critical mediator of septic shock comes primarily from experiments in which pretreatment of animals with anti-TNF antibodies reduces lethality [Beutler et al., *Science*, 229:869, (1985); Mathison et al., *J. Clin. Invest*, 81:1925 (1988)]. These reports suggest that interruption of the secretion of TNF caused by LPS or other factors would ameliorate the often lethal symptoms of sepsis.

Current concepts support the contention that the primary response of the host to LPS (including man) involves the recognition of LPS by cells of the monocyte/macrophage lineage, followed by the rapid elaboration of a variety of cell products including the general group known as cytokines. Other cell types believed to participate in sepsis and in particular in the response to LPS are polymorphonuclear leukocytes (PMN) and endothelial cells; each of these cell types are also capable of responding to LPS with the elaboration of potent inflammatory substances, and in the case of polymorphonuclear leukocytes, the elaboration of cytotoxic molecules.

Upon introduction of LPS into the blood, it may bind to a protein termed lipopolysaccharide binding protein (LBP). LBP is a 60 kD glycoprotein present at concentrations of less than 100 ng/ml in the serum of healthy animals and man. During the acute phase, LBP is synthesized by hepatocytes, and reaches concentrations of 30–50 ug/ml in serum. LBP can be purified from acute phase human and rabbit serum [Tobias et al. *J. Exp. Med.*, 164:777–793 (1986)]. LBP recognizes the lipid A region of LPS and forms high affinity, 1:1 stoichiometric complexes with both rough and smooth form LPS [Tobias et al., *J. Biol. Chem.*, 264:10867–10871 (1989)]. LBP bears N-terminal sequence hemology with the LPS-binding protein known as bactericidal permeability-increasing factor, (BPI) [Tobias et al., *J. Biol. Chem.*, 263:13479–13481, (1988)]. BPI is stored in the specific granules of PMN [Weiss et al., *Blood*, 69:652-659, (1987)] and kills gram-negative bacteria by binding LPS and disrupting the permeability barrier [Weiss et al., *J. Immunol.*, 32:3109–3115, (1984)]. In contrast to BPI, LBP is not directly cytotoxic for gram-negative bacteria [Tobias et al., *J. Biol. Chem.*, 263:13479–13481, (1988)] and its precise biological function has been obscure.

By way of further background, the cells of the monocyte/macrophage lineage perform diverse immune function including the phagocytosis of microorganisms, the uptake of antigenic material and its presentation in a form which is stimulatory to helper T cells. They are probably also involved in the immune surveillance against tumors and they secrete some complement components and cytokines. Surface membrane antigens play a critical role in regulating these activities. Several monocyte/macrophage surface antigens have been identified and their molecular weight has been determined. One such antigen, CD14, is a 55-kD glycoprotein expressed by monocytes, macrophages, and activated granulocytes. It is recognized by a number of monoclonal antibodies (mAbs) including MO2, MY4, 3C10 and LEUM3. Although no biological function has yet been ascribed to CD14, its restricted expression on mature cells suggests an important effector function. The nucleotide sequence of the gene encoding the monocyte cell surface differentiation antigen CD14 has been determined and the amino acid residue sequence of CD14 has been deduced therefrom [Ferrero et al., *Nucleic Acids Research*, 16:4173 (1988)].

Human serum contains trace quantities of the protein lipopolysaccharide binding protein (LBP), and it has recently been shown that this protein interacts first with LPS (endotoxin) and then with CD14 on the surface of phagocytes to provoke cellular responses that underlie the phenomenon of septic shock [Wright et al., *Science*, 249:1431–1433 (1990)]. However, several observations suggested that, while LBP can participate in the binding of LPS and CD14, it may not be the only protein involved. Three observations have been noted that commend this conclusion: (1) the addition of purified LBP to human mononuclear cells did not restore the ability of these cells to synthesize TNF in response to physiological doses of LPS as observed in the presence of serum; (2) LBP is an acute phase reactant that is present in satisfactory quantities during the acute phase response, but sufficient quantities may not be present in healthy individuals to explain their responses to LPS; and (3) "LPB-like" activity has been assayed by measuring the ability of solutions to mediate the binding of LPS to macrophages, and very high levels in serum from healthy individuals have been found, which levels are far too high to be explained by the content of LBP in the serum. These observations were the incentive for seeking a novel molecule in human serum that had the properties of binding LPS and CD14.

In copending U.S. application Ser. No. 07/473,609, now abandoned, a molecule named "septin" by the Applicant was identified that was found to function as an opsonin, and that exhibited the following profile of characteristics:

(a) the opsonin is capable of binding to lipopolysaccharide (LPS) to form a complex that is recognized by a receptor or monocytes, macrophage cells and polymorphonuclear cells (PMNs);

(b) the opsonin possess an apparent molecular weight of about 90 kD as determined by SDS-PAGE;

(c) the opsonin is present in high levels in normal serum, and enhances the elaboration of TNF by monocytes in response to LPS;

(d) a complex of the opsonin and LPS stimulates PMN activity, promotes increased PMN adhesion to endothelium, causes PMN degranulation and upregulates the expression of the adhesion molecule CR3; and (e) the opsonin is unable to bind to the receptor CD14 when first bound in a complex with Lipid IVa, the biosynthetic precursor of LPS.

The apparent involvement of the molecule with host response to invasion and other traumatic events forecast an active role for the molecule in both diagnostic and therapeutic applications related to infection and trauma. Subsequent study of the molecule has revealed additional structural and functional characteristics that enhance the understanding of the molecule and, in turn, are believed to broaden its utility. It is therefore toward the increased understanding and application of the molecule that the present Application is directed.

SUMMARY OF THE INVENTION

In accordance with the present invention, a molecule named by the applicant herein "septin" has been discovered that functions as an opsonin. The opsonin comprises a protein in purified form that as its primary affirmative characteristics, is capable of binding to lipopolysaccharide to form a complex recognized by a receptor on monocytes, macrophage cells and polymorphonuclear cells; and that possesses an apparent molecular weight of about 90 kD as determined by SDS-PAGE analysis.

The present opsonin possesses additional affirmative characteristics, among them that it is present in high levels in normal serum, and enhances the elaboration of TNF by monocytes in response to lipopolysaccharide. Also, when the opsonin is in a complex with lipopolysaccharide, it stimulates polymorphonuclear cell activity, promotes the increased adhesion of polymorphonuclear cells to endothelium, upregulates the expression of the adhesion molecule CR3, and causes the degranulation of said polymorphonuclear cells.

Further properties of the present opsonin include its inability to bind to the receptor CD14 when first bound in a complex with the biosynthetic precursor of lipopolysaccharide known as Lipid IVa.

While the complete role that the present isolate plays in the cascade of reactions to host invasion is as yet undefined, its participation in the elicitation of certain of the activities and conditions associated with mobilization against host invasion is clear. Accordingly, the opsonin possesses the potential for use as a diagnostic tool to identify and perhaps differentiate between various stimuli whether invasive or idiopathic, by the activation of the present opsonin that such stimuli may promote.

The present opsonin possesses certain characteristics in common with lipopolysaccharide binding protein (LBP). Like LBP, the present opsonin is serum-derived and binds LPS-coated particles and mediates their attachment to macrophages in a CD14-dependent fashion. Unlike LBP, however, the present opsonin has a different molecular weight from LBP, is present in normal serum in high levels, and, for example, may be present in amounts ranging up to on the order of about 4 µg/ml. This is significantly greater than the known opsonin LBP, which as indicated earlier, is present in a maximal concentration of less than 100 ng/ml in healthy individuals. The present opsonin is also significantly more potent than LBP, and for example, exhibits as much as 20-fold greater activity in the mediation of the binding of complexes with LPS-coated erythrocytes with macrophage cells. Particularly, maximal binding of lipopolysaccharide to monocytes, macrophage cells and polymorphonuclear cells as measured by the binding activity of LPS-coated erythrocytes to human macrophage cells may be achieved by the presence and binding with such erythrocytes of a concentration of no more than about 0.05 µg/ml of the opsonin.

Figure 1:
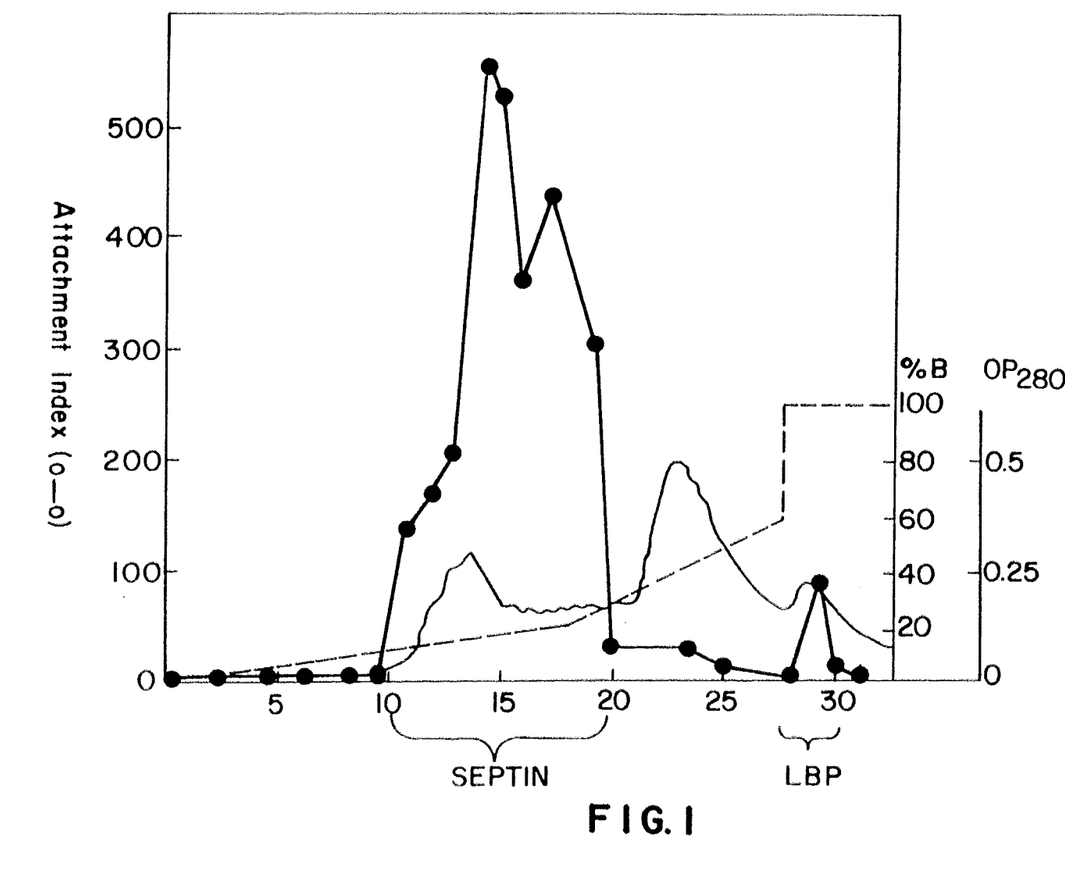

The present opsonin is also distinct from LBP by the peak of activity that it exhibited in elution with NaCl, as described in Example 1 infra., and as shown in FIG. 1. Particularly, the present opsonin was eluted with BioRex resin with an NaCl gradient and displayed a prominent peak at about 200 mM NaCl, in contrast to a far smaller peak for LBP that appeared at >500 mM NaCl. Further discussion of these data appears in Example 1.

Further study and characterization of the opsonin of the present invention reveals that it comprises a complex of a protease and a substrate for the protease. More particularly, the substrate appears to bear some structural similarity to human protein C inhibitor (PCI). The opsonin is now theorized to participate in a protease cascade in conjunction with its interaction with LPS, thereafter is believed to form a complex and interact with CD14. As such, the exact molecular weight and structure of the perceived components of the opsonin are yet to be determined, and it is theorized that the opsonin may be derived from several proteases and proteins which interact.

The opsonin of the invention has been studied by exposure to protease inhibitors, and antibodies to the opsonin have likewise been raised. The data presented hereinafter reveal that the activity of the opsonin is substantially diminished by contact with protease inhibitors. Particular protease inhibitors that have been found to exert this activity are selected from the group consisting of antipain, leupeptin, benzamidine, chymostatin, pepstatin A, aprotinin and mixtures of these.

The present invention likewise extends to antibodies developed to the opsonin, including antibodies that may be raised against a component of the protease cascade that appears to give rise to the opsonin. An exemplary antibody to the opsonin was raised in rabbits and has been determined to completely block the binding of LPS to monocytes (MO). Both monoclonal and polyclonal antibodies to the opsonin are contemplated and includeable herein.

The present opsonin was initially identified and characterized and found to comprise a 90 kilodalton (kD) protein on sodium dodecyl sulfate polyacrylamide gel electrophoresis (SDS-PAGE). As set out above, the opsonin may be prepared by isolation and purification from body fluid and particularly serum. The serum or other fluid may be subjected to a series of known isolation techniques, whereupon the opsonin may be recovered. The present invention naturally contemplates alternate means for preparation of the opsonin, including where applicable known genetic replicarive techniques, and the invention is accordingly intended to cover such synthetic preparations within its scope.

The isolation of the cDNA amino acid sequence will facilitate the reproduction of the opsonin by recombinant genetic techniques as discussed in detail hereinafter. Thus, the DNA sequence encoding the present opsonin or analogs thereof can be used to construct vectors for expression in host systems by recombinant DNA techniques.

The invention further includes a method for detecting idiopathic or invasive stimuli on the basis of their ability to elicit the activities affected by the present opsonin. In particular, invasive stimuli could be identified and detected by their ability to bind with the present opsonin and to form a complex recognized by a receptor on monocytes, macrophage cells and polymorphonuclear cells. In this method, macrophage cells derived for example, from the THP1 cell line could be treated with/exposed to a number of known stimulator materials such as endotoxin, trypanosomes or the like, as a control, while parallel cellular samples could be treated with or exposed to an extract of material from the presumed situs of the infectire stimulus. All samples could thereafter be incubated in accordance with the methods described above, and thereafter subjected to the sequence of separation techniques also defined, whereupon testing of the resulting isolates derived from the control and unknown samples could be compared to determine whether a macrophage activating binding complex involving the opsonin, if any, is developed and is identical or even similar either structurally or functionally.

In similar fashion, an assay system for screening of potential drugs effective to counteract the opsonin may be prepared. In one instance, the test drug could be administered to a macrophage sample with the opsonin and a quantity of lipopolysaccharide present, to determine its effect upon the binding activity of the opsonin to either the LPS or the macrophage. In an alternate procedure, the opsonin may be introduced into a cellular test system in which the opsonin is known to be active, and the prospective drug may also be introduced to the same cell culture and the culture may thereafter be examined to observe any changes in the activity of the opsonin in comparison with the addition of the prospective drug alone, or the effect of added quantities of the known opsonin.

The present invention also relates to a method for detecting the presence of stimulated, spontaneous, or idiopathic pathological states in mammals, by measuring the activity and presence of the opsonin of the present invention. More particularly, the activity of the opsonin may be followed directly by the assay techniques discussed later on, through the use of an appropriately labeled quantity of the opsonin. Alternately, the opsonin can be used to raise binding partners or antibodies that could in turn, be labeled and introduced into a medium such as serum, to test for the presence of opsonin therein, and to thereby assess the state of the host from which the medium was drawn.

Thus, both the opsonin and any antibodies that may be raised thereto, are capable of use in connection with various diagnostic techniques, including immunoassays, such as a radioimmunoassay, using for example, an antibody to the opsonin that has been labeled by either radioactive addition, reduction with sodium borohydride, or radioiodination.

In an immunoassay, a control quantity of the opsonin, its antibody, or the like may be prepared and labeled with an enzyme, a specific binding partner and/or a radioactive element, and may then be introduced into a blood sample of a mammal believed to be undergoing invasion. After the labeled material or its binding partner(s) has had an opportunity to react with sites within the sample, the resulting mass may be examined by known techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, fluorospectrophotometric or gasometric techniques known in the art.

The present invention includes an assay system which may be prepared in the form of a test kit for the quantitative analysis of the extent of the presence of the opsonin. The system or test kit may comprise a labeled component prepared by one of the radioactive and/or enzymatic techniques discussed herein, coupling a label to the opsonin; and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the opsonin, antibodies to the opsonin, or upon agents or other drugs determined to possess the same or an antagonistic activity. A first therapeutic method is associated with the prevention of the manifestations of conditions following from the binding activity of the opsonin, such as inflammation and fever, and comprises administering either an antibody to the opsonin, an agent capable of modulating the production and/or activity of the opsonin, or an agent not an antibody to the opsonin that is capable of acting as an antagonist to the opsonin, either individually or in mixture with each other in an amount effective to prevent the development of those conditions in the host.

More specifically, the therapeutic method generally referred to herein could include the method for the treatment of sepsis, inflammation and/or fever by the administration of pharmaceutical compositions that may comprise effective quantities of antibodies to the opsonin, or other equally effective drugs developed for instance by a drug screening assay prepared and used in accordance with a further aspect of the present invention.

A variant embodiment of this therapeutic method could include initially detecting the presence and activity of the opsonin and thereafter administering the appropriate pharmaceutical composition.

Accordingly, it is a principal object of the present invention to provide an opsonin in purified form that exhibits certain characteristics and activities associated with the host response to invasive stimuli in mammals.

It is a further object of the present invention to provide methods for the preparation of the opsonin, including recombinant means.

It is a further object of the present invention to provide a method for detecting the presence of the opsonin in mammals in which invasive, spontaneous, or idiopathic pathological states such as infection are suspected to be present.

It is a further object of the present invention to provide a method and associated assay system for screening substances such as drugs, agents and the like, potentially effective in either mimicking the activity or combating the adverse effects of the opsonin in mammals.

It is a still further object of the present invention to provide a method for the treatment of mammals to control the amount or activity of the opsonin, so as to alter the adverse consequences of such presence or activity.

It is a still further object of the present invention to provide a method for the treatment of mammals to promote the amount or activity of the opsonin, so as to treat or avert the adverse consequences of invasive, spontaneous or idiopathic pathological states.

It is a still further object of the present invention to provide pharmaceutical compositions for use in therapeutic methods which comprise or are based upon the opsonin or its binding partner(s), or upon agents or drugs that control the production, or that mimic or antagonize the activities of the opsonin.

Other objects and advantages will become apparent to those skilled in the art from a review of the ensuing description which proceeds with reference to the following illustrative drawings.

BRIEF DESCRIPTION OF THE DRAWINGS

FIG. 1 is a graph depicting the purification of the present opsonin septin. Human plasma was exposed to BioRex in batch fashion, then poured into a column and eluted with the NaCl gradient illustrated. $OD_{280}$ and activity of fractions are illustrated. Septin-rich fractions, pooled as shown, possessed a dominant 90 kD band and >10 lower molecular weight bands. Subsequent purification on Mono Q yielded a homogeneous preparation shown in the inset.

FIG. 2 is a graph depicting how septin-LPS complexes cause increased expression of CR3 on PMN. Suspensions of PMN were incubated for 30 minutes at 37° C. with doses of LPS (Re) in the presence and absence of the opsonin septin, and expression of CR3 on the cell surface was determined by FACS, as described in Lo et al, *J. Immunol.*, 143(10):3325-3329 (1989). Expression of FcRIII was unchanged in this period.

FIG. 3 is a graph depicting how septin-LPS complexes cause increased binding activity of CR3 on PMN. PMN were incubated in assay plates for 45 minutes at 37° C. with doses of LPS (Re) in the presence and absence of septin. The resulting monolayers were washed and incubated for 30 minutes with C3bi-coated erythrocytes, and the attachment index was enumerated as the number of erythrocytes bound per 100 phagocytes, as described in Wright et al., *J. Immunol.*, 136(5):1759-1764 (1986).

DETAILED DESCRIPTION

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "stimulus" and its plural as used herein are intended to apply to invasive events such as infection, as well as conditions caused by wounding, and to idiopathic or spontaneous states that may for example, originate from cellular or metabolic derangements or other causes.

The term "opsonin" as used throughout the present application and claims refers to protein material having the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the opsonin. Also, the term "opsonin" is intended to include within its scope proteins specifically recited herein as well as all substantially homologous analogs and allelic variations.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adeninc, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will-often, but not always, contain "TATA" boxes and "CAT" boxes. Prokaryotic promoters contain Shine-Dalgarno sequences in addition to the −10 and −35 consensus sequences.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO 0 116 201, publication date 12 Jan. 1983; U.S. patent application Ser. No. 522,909, filed 12 Aug. 1983, now abandoned). Further, the alpha-factor leader and its analogs have been found to secrete heterologous proteins from a variety of yeast, such as Saccharomyces and Kluyveromyces, (EPO 88312306.9 filed 23 Dec. 1988; U.S. patent application Ser. No. 139,682, filed 30 Dec. 1987, now abandoned, and EPO Publication No. 0,301 669, publication date 1 Feb. 1989).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger. DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

An "antibody" is any immunoglobulin, including antibodies and fragments thereof, that binds a specific epitope. The term encompasses, inter alia, polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')2 and F(V), which portions are preferred for use in the therapeutic methods described herein.

Fab and F(ab')2 portions of antibody molecules are prepared by the proteolytic reaction of papain and pepsin, respectively, on substantially intact antibody molecules by methods that are well-known. See for example, U.S. Pat. No. 4,342,566 to Theofilopolous et al. (The disclosures of the art cited herein are hereby incorporated by reference.). Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimetic) monoclonal antibody.

The phrase "substantially simultaneously" is used herein to mean within a time period sufficient to produce concurrent results; e.g., bacterial lysis as a result of antibiotic administration and amelioration or prevention of symptoms of sepsis that may occur as a result of that lysis by administration of an anti-opsonin antibody, peptide analog, or a subcombination or combination thereof, as described herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the plasma level of TNF, or other feature of septic shock such as elevated blood pressure, fever or white cell count.

In its primary aspect, the present invention concerns the isolation and identification of a newly discovered particular factor hereinafter referred to as the opsonin, that has been found to be present in serum or plasma, and that participates in the binding of stimulator materials that characteristically accompany an invasive stimulus such as lipopolysaccharide (LPS), to monocytes, macrophage cells and polymorphonuclear leukocytes such as bacteria, virus, certain tumors, protozoa and other toxins such as endotoxin, or an idiopathic state.

Previous studies by the applicant have shown that the serum protein, LBP, binds to LPS-coated erythrocytes and mediates their binding to the antigen CD14 on human macrophages, and that the macrophage-LPS complex so formed, in turn, activates the elaboration of certain factors such as TNF, that appear to mediate and mobilize the host against the invasive stimulus. To determine if additional serum proteins with the ability to bind LPS and CD14 and thereby initiate this catabolic response exist, human serum was fractionated and each fraction assayed for its capacity to mediate interaction of LPS-coated erythrocytes with macrophages. The result of this investigation as set forth herein is the discovery of the LPS-binding opsonin that has been named herein "septin".

As stated earlier, the opsonin comprises a protein in purified form that as its primary affirmative characteristics, is capable of binding to lipopolysaccharide to form a complex recognized by a receptor on monocytes, macrophage cells and polymorphonuclear cells; and that possesses an apparent molecular weight of about 90 kD as determined by SDS-PAGE analysis.

More particularly, the opsonin of the invention has now been determined to comprise a complex of a protease and a substrate for such protease. This determination is consistent with the present characterization of the opsonin as participating in a protease cascade that includes interaction of the opsonin with LPS and the formation of a complex capable of binding with CD14. While the opsonin appears to possess an apparent molecular weight of about 93 kilodaltons (kD), the exact attribution of the molecular weight to the respective components believed to comprise the opsonin is as yet not fully determined. It is theorized that the substrate for the protease, which appears to possess some structural similarity to protein C inhibitor (PCI), a plasma protein of the serpin family; however, experimentation with a sample of protein C inhibitor has revealed no such similarity in activity. Further investigation of the interaction of the protease or proteases with the substrate will follow in an effort to elucidate the origins of the activity of the complex molecule from its putative precursor components.

As a result of the determination that the present opsonin is a complex of a protease and a substrate for such protease, certain experimentation has determined that the activity of the opsonin may be blocked by the action of protease inhibitors. More particularly, certain protease inhibitors have been examined, and such inhibitors showing activity against the present opsonin may be selected from the group consisting of antipain, leupeptin, benzamidine, chymostatin, pepstatin A, aprotinin and mixtures of these. Accordingly, methods for blocking the action of the opsonin and any consequent diagnostic or therapeutic utilities to which such methods pertain, would comprise the administration or application, as the case may be, of the noted protease inhibitors.

The present opsonin possesses additional affirmative characteristics, among them that it is present in high levels in normal serum, and enhances the elaboration of TNF by monocytes in response to lipopolysaccharide. Also, when the opsonin is in a complex with lipopolysaccharide, it stimulates polymorphonuclear cell activity, promotes the increased adhesion of polymorphonuclear cells to endothelium, upregulates the expression of the adhesion molecule CR3, and causes the degranulation of said polymorphonuclear cells.

Further properties of the present opsonin include its inability to bind to the receptor CD14 when the opsonin is first bound in a complex with the biosynthetic precursor of lipopolysaccharide known as Lipid IVa.

The present invention contemplates methods of treating and/or preventing one or more of the symptoms of sepsis, particularly those associated with a transient increase in the blood level of TNF, such as fever, hypotension, neutropenia, leukopenia, thrombocytopenia, shock and multiple organ failure. Patients in need of such treatment include those at risk for or suffering toxemia, such as endotoxemia resulting from a gram-negative bacterial infection, serpent venom poisoning, hepatic failure, and the like. In addition, some patients having a gram-positive bacterial, viral or fungal infection display the symptoms of sepsis and may benefit from a therapeutic method of this invention. Patients particularly able to benefit from the present invention are those suffering infection by *E. coli, Haemophilus influenza* B, *Neisseria meningitides, staphylococci,* or *pneumococci.* Patients at risk for sepsis include those suffering burns, gunshot wounds, renal or hepatic failure due to chemical poisoning or abuse, and the like.

Thus, in one embodiment, the present invention contemplates a method of ameliorating one or more of the symptoms of sepsis by administering to a patient in need of such therapy a therapeutically effective amount of an anti-opsonin antibody. Preferred therapeutically effective amounts for the agents used herein as active ingredients include those described hereinafter. A clinically significant increase in the plasma level of TNF is an increase to at least about 25 pg/ml. Methods for determining the plasma TNF levels are well-known in the art, particularly preferred methods being those described herein.

It should be noted that levels of TNF in normal healthy humans or in laboratory animals are estimated to be no more than about 10 pg/ml, a value that is at the limit of detection by the most sensitive assays for TNF [Michie et al., *New Eng. J. Med.* 318:1481–1486 (1988); Mathison, et al., *J. Clin. Invest.* 81:1925 (1988) and Waage et al., *Laucet,* 1:355–357 (1987)]. Following exposure to LPS, the levels of TNF have been shown to rise 10–20 fold to levels of up to 400 pg/ml (vide Supra). Recently, a good correlation has been shown between serum TNF levels and fatal outcome in infection with gram-negative, LPS-containing meningococcal bacteria [Waage et al., *Lancet,* 1:355–357 (1987)]. Further, in animal models of sepsis with subhuman primates, similar increases in TNF were noted and these changes were directly correlated with lethality [Tracey et al., *Nature,* 330:662–664, (1987)].

As discussed earlier, the opsonin or its binding partner(s) or other ligands or agents exhibiting either mimicry or antagonism to the opsonin or control over its production, may be prepared in pharmaceutical compositions, with a suitable carrier and at a strength effective for administration by various means to a patient having a tissue infection or other pathological derangement, for the treatment thereof. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, including delivery in an irrigation fluid used to wash body wound areas, catheterizations and the like. Average quantities of the opsonin may vary and in particular should be based upon the recommendations and prescription of a qualified physician or veterinarian.

Also, antibodies including both polyclonal and monoclonal antibodies, and drugs that modulate the production or activity of the opsonin may possess certain therapeutic applications and may thus be utilized for the purpose of treating the effects of post infection attributable the action of the opsonin, such as inflammation and fever. In particular, the opsonin may be used to produce both polyclonal and monoclonal antibodies to itself in a variety of cellular media, by known techniques such as the hybridoma technique utilizing, for example, fused mouse spleen lymphocytes and myeloma cells. Suitable antibodies would also extend to antibodies that may be raised against a component of the protease cascade that gives rise to the opsonin, as well as to the perceived component parts of the opsonin, namely the protease and/or its substrate. Accordingly, antibodies to any of these antigens would interrupt the synthesis and/or activity of the opsonin and would thereby inhibit or block its action.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Bart virus. See, e.g., M. Schreier et al., "Hybridoma Techniques" (1980); Hammerling et al., "Monoclonal Antibodies And T-cell Hybridomas" (1981); Kennett et al, "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against opsonin peptides can be screened for various properties; i.e., isotype, epitope, affinity, etc. Of particular interest are monoclonal antibodies that neutralize the activity of opsonin. Such monoclonals can be readily identified in opsonin activity assays. High affinity antibodies are also useful in immunoaffinity purification of native or recombinant opsonin.

Preferably, the anti-opsonin antibody used in a therapeutic method of this invention is an affinity purified polyclonal antibody. More preferably, the antibody is a monoclonal antibody (mAb). In addition, it is preferable for the anti-CD14 antibody molecules used herein be in the form of Fab, Fab', F(ab')$_2$ or F(V) portions of whole antibody molecules.

Preferred monoclonal antibodies display an immunoreactivity for the opsonin that is similar to that of those produced by the above-described hybridomas. As used herein, the term "immunoreactivity" in its various grammatical forms refers to the concentration of antigen required to achieve a 50% inhibition of the immunoreaction between a given amount of the antibody and a given amount of the opsonin antigen. That is, immunoreactivity is the concentration of antigen required to achieve a B/B$_0$ value of 0.5, where B$_0$ is the maximum amount of antibody bound in the absence of competing antigen and B is the amount of antibody bound in the presence of competing antigen, and both B$_0$ and B have been adjusted for background. See Robard, *Clin. Chem.,* 20:1255–1270 (1974).

In another particular embodiment, the therapeutic method of the present invention comprises administering a therapeutically effective amount of an anti-opsonin antibody, preferably an affinity-purified polyclonal antibody, and more preferably a mAb. In addition, it is preferable for the anti-opsonin antibody molecules used herein be in the form of Fab, Fab', F(ab')$_2$ or F$_{(v)}$ portions or whole antibody molecules. Preferably, the amount of anti-opsonin antibody administered is sufficient to reduce by at least about 30 percent, preferably by at least 80 percent, an opsonin-LPS complex induced clinically significant increase in the blood level of TNF in a patient displaying at least one of the symptoms of sepsis. As previously discussed, patients capable of benefiting from this method include those suffering endotoxemia as a result of a gram-negative bacterial infection. Methods for isolating the opsonin and inducing anti-opsonin antibodies and for determining and optimizing the ability of an anti-opsonin antibody to inhibit the binding of opsonin-LPS complexes to CD14 and thereby inhibit opsonin-induced TNF secretions are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')2 portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with CD14 or an opsonin-binding portion thereof, or opsonin or a CD14-binding portion thereof.

It is preferred that the myeloma cell line be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-AgS8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with CD14 or the present opsonin and their ability to inhibit LPS-induced TNF secretion.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the Balb/c.

Methods for producing monoclonal anti-opsonin antibodies are also well-known in the art. See Niman et al., *Proc. Natl. Acad. Sci. USA*, 80:4949–4953 (1983). Typically, the present opsonin or a peptide analog is used either alone or conjugated to an immunogenic carrier, as the immunogen in the before described procedure for producing anti-CD14 monoclonal antibodies. The hybridomas are screened for the ability to produce an antibody that immunoreacts with the opsonin peptide analog and the present opsonin.

Patients at a risk for or exhibiting the symptoms of sepsis are capable of benefiting from the administration of therapeutic modalities known in the art to prevent or ameliorate those symptoms. Thus, the present invention contemplates administering a therapeutically effective amount of an anti-opsonin antibody, opsonin peptide analog, a subcombination or combination thereof, substantially simultaneously with therapeutic administration of a modality known to prevent or treat the symptoms of sepsis. For instance, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody having an immunologic specificity for TNF corresponding to that described by [Tracey et al., *Nature*, 330:662–664 (1987)].

Similarly, a therapeutic method of this invention can further include substantially simultaneous treatment with a steroid, such as cortisol, hydrocortisone and the like.

A patient exhibiting the symptoms of sepsis is usually treated with an antibiotic, typically an aminoglycoside such as gentamicin or a beta-lactim such as penicillin, cephalosporin and the like. Thus, a preferred therapeutic method includes administering a therapeutically effective amount of an anti-opsonin antibody, a peptide analog or subcombination thereof as described herein, substantially simultaneously with administering a bactericidal amount of an antibiotic. The phrase "bactericidal amount" is used herein to mean an amount of sufficient to achieve a bacteria-killing blood concentration in the patient receiving the treatment. The bactericidal amount of antibiotics generally recognized as safe for administration to humans is an amount well-known in the art and varies, as is also well-known, with the antibiotic and the type of bacterial infection being treated.

In preferred embodiments, administration of an anti-opsonin antibody, peptide analog or combination thereof as described herein occurs within about 48 hours, preferably within about 12–36 hours, more preferably within about 2–8 hours and most preferably substantially concurrently with administration of the antibiotic.

Antibiotics useful in practicing the present invention include those antibiotic, antibacterial and antiseptic agents having formulations described in the Physicians' Desk Reference, Huff, B.B. ed., Medical Economics Company, Inc., Oradell, N.J. (1989). In another embodiment, the present invention contemplates administering a therapeutically effective amount of CD14, preferably a soluble portion thereof that binds LPS-opsonin complexes, alone or in subcombination or combination with a therapeutically effective amount of an anti-TNF antibody, an anti-opsonin antibody, and an antibiotic. The cDNA coding for CD14 and its deduced amino acid residue sequence are well-known in the art. See Goyert et al, *Science*, 239:497–500 (1988), Ferrero et al., *Nuc. Acids Res.*, 16:4173 (1988), and Bazil et al., *Eur. J. Immunol.*, 16:1583–1589 (1986).

The present invention further contemplates therapeutic compositions useful in practicing the therapeutic methods of this invention. A subject therapeutic composition includes, in admixture, a pharmaceutically acceptable excipient (carrier) and one or more of an anti-opsonin antibody, or polypeptide analog thereof, as described herein as an active ingredient. In preferred embodiments, the composition comprises an antibody or antigen capable of inhibiting either the binding of LPS to the present opsonin, or the binding of LPS-opsonin complexes to CD14. A possible antigenic antagonist is Lipid IVa.

In another preferred embodiment, the compositions comprise an anti-opsonin antibody, preferably a mAb, that inhibits the binding of LPS-opsonin complexes to CD14. Preferred therapeutic compositions further include an effective amount of the anti-opsonin antibody of the invention and one or more of the following active ingredients: an antibiotic, asteroid, and anti-TNF antibody an a TNF antagonist. Exemplary formulations are given below:

| Ingredient | Dose (mg/ml) |
| --- | --- |
| Formulation A | |
| gentamicin (sulfate) | 40 |
| anti-opsonin antibody | 10 |
| sodium bisulfite USP | 3.2 |
| disodium EDTA USP | 0.1 |
| water for injection q.s.a.d. | 1.0 ml |
| Formulation B | |
| anti-TNF antibody | 10 |
| anti-opsonin antibody | 10 |
| sodium bisulfite USP | 3.2 |
| disodium EDTA USP | 0.1 |
| water for injection q.s.a.d. | 1.0 ml |

In another embodiment, the present invention contemplates a therapeutic composition useful in treating sepsis comprised of CD14 or an opsonin-binding soluble portion thereof in a pharmaceutically acceptable carrier. Preferably, the composition further includes a therapeutically effective concentration of one or more of an anti-TNF antibody, an anti-opsonin antibody and an antibiotic.

The preparation of therapeutic compositions which contain polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of CD14 or LPS-opsonin complex binding capacity desired. Precise amounts of active ingredient required to be administered depend on the judgment of the practitioner and are peculiar to each individual. However, suitable dosage ranges are of the order of 0.1 to 20, preferably about 0.5 to about 10, and more preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nano molar to ten micromolar in the blood are contemplated.

As used herein, "pg" means picogram, "ng" means nanogram, "ug" or "µg" mean microgram, "mg" means milligram, "ul" or "µl" mean microliter, "ml" means milliliter, "l" means liter.

It is further intended that opsonin analogs may be prepared from nucleotide sequences of the opsonin derived within the scope of the present invention. Analogs, such as fragments, may be produced, for example, by pepsin digestion of opsonin. Other analogs, such as muteins, can be produced by standard site-directed mutagenesis of opsonin coding sequences. Analogs exhibiting "opsonin activity" may be identified by known in vivo and/or in vitro assays.

As mentioned above, a DNA sequence encoding opsonin can be prepared synthetically rather than cloned. The DNA sequence can be designed with the appropriate codons for the opsonin amino acid sequence. In general, one will select preferred codons for the intended host if the sequence will be used for expression. The complete sequence is assembled from overlapping oligonucleotides prepared by standard methods and assembled into a complete coding sequence. See, e.g., Edge Nature, 292:756 (1981); Nambair et al. Science, 223:1299 (1984); Jay et al., J. Biol. Chem. 259:6311 (1984).

Synthetic DNA sequences allow convenient construction of genes which will express opsonin analogs or "muteins". Alternatively, DNA encoding muteins can be made by site-directed mutagenesis of native opsonin genes or cDNAs, and muteins can be made directly using conventional polypeptide synthesis.

Site-directed mutagenesis is generally used to create analogs from a complete coding sequence. Site-directed mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The present invention also relates to a variety of diagnostic applications, including methods for detecting the presence of invasive stimuli by reference to their ability to elicit the activities which are affected by the present opsonin. As mentioned earlier, the opsonin can be used to produce antibodies to itself by a variety of known techniques, and such antibodies could then be isolated and utilized as in tests for the presence of the opsonin in suspect mammalian hosts.

Antibody(ies) to the opsonin can be produced and isolated by standard methods including the well known hybridoma techniques. For convenience, the antibody(ies) to the opsonin will be referred to herein as $Ab_1$ and antibody(ies) raised in another species as $Ab_2$.

The presence of opsonin activity in mammals can be ascertained by the usual immunological procedures applicable to such determinations. A number of useful procedures are known. Three such procedures which are especially useful utilize either the opsonin labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Ops" stands for the opsonin:
A. $Ops^* + Ab_1 = Ops^*Ab_1$
B. $Ops + Ab^* = OpsAb_1^*$
C. $Ops + Ab_1 + Ab_2^* = OpsAb_1Ab_2^*$ The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody" or "DASP" procedure.

In each instance, the inflammatory opsonin forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-opsonin antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The opsonin or its binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the opsonin may be radiolabeled and combined, for example, with LPS, after which binding studies would be carried out using for example, recently purified neutrophils. Solutions would then be prepared that contain various quantities of labeled and unlabeled opsonin and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of opsonin in a suspected mammalian host. In accordance with the testing techniques discussed above, one class of such kits will contain at least the labeled opsonin or its binding partner, for instance an antibody specific thereto, and directions, of course, depending upon the method selected, e.g., "competitive" "sandwich" "DASP" and the like. The kits may also contain peripheral reagents such as buffers, stabilizers, etc.

Accordingly, a test kit may be prepared for the demonstration of the reaction of a mammalian host to invasive stimuli, comprising:

(a) a predetermined amount of at least one labeled immunochemically reactive component obtained by the direct or indirect attachment of the present opsonin or a specific binding partner thereto, to a detectable label;

(b) other reagents; and (c) directions for use of said kit.

More specifically, the diagnostic test kit may comprise:

(a) a known amount of the opsonin as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the opsonin to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding With at least one of the binding partners of at least one of the component(s) to be determined; and (c) directions for the performance of a protocol for the detection and/or determination of one or more components of an immunochemical reaction between the opsonin and a specific binding partner thereto.

In accordance with the above, an assay system for screening potential drugs effective to modulate the activity of the opsonin may be prepared. The opsonin may be introduced into a cellular test system such as neutrophils with 100 pg/ml LPS, and the prospective drug may also be introduced into the resulting cell culture, and the culture thereafter examined to observe any changes in the activity of the opsonin, due either to the addition of the prospective drug alone, or due to the effect of added quantities of the known opsonin.

More particularly, a drug assay could be conducted by culturing a colony of test cells such as the cell line THP1, which has a receptor for the complex of the opsonin and LPS, in a medium containing the opsonin and LPS. The drug under test could be added to the resulting culture and the reactivity of the opsonin with the receptor on the test cells could thereafter be measured to determine whether the prospective drug possessed any activity in the inhibition of the binding of the opsonin to either LPS or to the receptor.

The following examples set forth the details of the isolation and identification of the present opsonin, and observations noted as to its activity, defining both the distinctions and similarities in activity between the present opsonin and those factors identified earlier both by applicant and by others in the field. Naturally, the specific materials and techniques set forth hereinafter are exemplary only and may vary, so that the following is presented as illustrative but not restrictive of the present invention.

EXAMPLE 1

Purification of Septin

Previous studies by the applicant have shown that the serum protein, LBP, binds to LPS-coated erythrocytes and mediates their binding to CD14 on human macrophages. To determine if additional serum proteins with the ability to bind LPS and CD14 exist, human serum was fractionated and its capacity assayed to each fraction to mediate interaction of LPS-coated erythrocytes with macrophages.

Human plasma and fractionated samples of plasma were diluted in PBS containing 1 mM EDTA and incubated with LPS-coated erythrocytes (ELPS) and human macrophages as previously described for 15 minutes at 0° C., then an additional 15 minutes at 20° C. The binding of erythrocytes to macrophages was then scored as attachment index, the number of erythrocytes bound per 100 phagocytes.

Materials and Methods 250 ml of fresh frozen human Plasma (Greater New York Blood Center) was brought to 2 mM EDTA and shaken at 4° C. overnight with 15 mls of packed, equilibrated, BioRex 70 resin. The resin was washed twice and packed into a column. Elution was carried out by washing with 100 mls of buffer A (50 mM Phosphate, pH 7.3, 40 mM NaCl, 2mM EDTA), followed by a gradient of buffer A mixed with Buffer B (Buffer A containing 1.0 M NaCl; see FIG. 1). Additional studies have indicated that Heparin-Sepharose binds septin, and that septin can be eluted with sodium chloride. Heparin-sepharose may be substituted for BioRex in this procedure.

Fractions active in the bioassay were pooled and dialyzed against 20 mM Tris pH 8.5. The pooled samples were then applied to a Mono Q column and eluted with a gradient of buffer from 0–1 M NaCl. Fractions with activity were again pooled and analyzed by electrophoresis.

Results

Dilutions of human plasma (or serum) up to 1:200 exhibit significant activity when assayed for the ability to mediate binding of ELPS to macrophages. Plasma did not influence binding of E to MO unless the E were coated with LPS, and all the plasma-mediated binding of ELPS to MO was inhibited by the anti-CD14 mAb, 3C10. This assay thus detects molecules that bind LPS and CD14. The capacity of plasma to mediate binding of ELPS is completely lost after incubation of the plasma with BioRex, indicating that this ion exchange resin quantitatively adsorbs the active molecules from plasma (data not shown).

Isolation of Septin

Elution of the BioRex with a gradient of NaCl gave rise to two peaks of activity, the first centered at approximately 200 mM NaCl, and a second at >500 mM NaCl (FIG. 1). The second peak has the reported elution characteristics of LBP, and further purification of this material on Mono Q yielded a 60 kD protein with the characteristics of LPB. However, LPB accounted for less than 4% of the activity of plasma. The major peak, accounting for >96% of the activity of plasma was further purified on a Mono Q column.

Elution with a gradient of NaCl gave rise to a single peak of activity at 190 mM NaCl. Further purification on a Superose 10 sizing column resulted in the isolation of a single molecular species. We have named this material septin. Analysis of dilutions of septin showed that the material eluted from Mono Q contained less than 1% of the initial activity, indicating that substantial loss of activity occurred upon chromatography on Mono Q.

Properties of Septin

Analysis of septin by SDS-PAGE reveals a single band of 90,000 (±3,000) Daltons. Septin mediates very avid binding of ELPS to macrophages. The concentration of septin needed for maximal binding is <0.05 µg/ml. Previous studies showed that 1 µg/ml of LBP is necessary for comparable binding [Wright et al., *J. ExD. Med.*, 170:1231-1241 (1989)]. Thus, septin is 20-fold more active than LBP in mediating the interaction of ELPS with macrophages.

All of the septin-mediated binding of ELPS to macrophages is blocked by the anti-CD14 mAb, 3C10, indicating that CD14 is the receptor responsible for recognizing septin-LPS complexes. Pretreatment of ELPS but not macrophages with septin results in adhesion, indicating that septin binds to LPS and that CD14 recognizes septin-LPS complexes, not septin alone.

EXAMPLE 2

Mononuclear Cells

One of the activities that the opsonin septin was speculated to possess is the ability to promote and enhance the ability of monocytes to produce and elaborate TNF in response to invasive stimuli such as LPS challenge. This hypothesis was tested by the following experiment.

Accordingly, mononuclear cells were isolated from fresh human blood on Ficoll gradients and suspended to $2 \times 10^6$ cells/ml in RPMI containing 0.5 mg/ml human serum albumin, 0.5 u/ml Aprotinin, and the indicated doses of Re endotoxin. After a 16 hour incubation, TNF in the supernatant was measured by a sandwich RIA. The results are set forth in Table I, below.

TABLE I

| Secretion of TNF by Human Mononuclear Cells | | |
|---|---|---|
| | TNF Production (ng/ml) | |
| LPS (ng/ml) | −Septin | +Septin (1 µ/ml) |
| 0 | 0.07 | 0.20 |
| 0.01 | 0.10 | 0.84 |

TABLE I-continued

| Secretion of TNF by Human Mononuclear Cells | | |
|---|---|---|
| | TNF Production (ng/ml) | |
| LPS (ng/ml) | −Septin | +Septin (1 µ/ml) |
| 0.05 | 0.20 | 1.35 |

From the above, it can be seen that TNF production which is known to be promoted by LPS, is substantially enhanced by the presence of both LPS and septin. While 1 µg/ml of septin alone accounted for a trebling of TNF production, the presence of the same amount of septin in combination with 0.01 ng/ml of LPS resulted in a more than eight-fold increase over the presence of the same amount of LPS alone. Similar enhancement was evident in the instance of 0.05 ng/ml LPS and the same concentration of septin, where a greater than seven-fold increase was noted.

EXAMPLE 3

Stimulation of PMN

Reports in the literature regarding the activities and characteristics of polymorphonuclear cells (PMN) suggest that low and variable amounts of CD14 are expressed on PMN. The expression of CD14 on PMN has been confirmed, showing that expression is upregulated two-to three-fold by degranulating stimuli such as GM-CSF, GCSP, and fNLLP. The CD14 on PMN is capable of mediating the binding of ELPS in the presence of either LBP or septin, and binding is increased 2- to 3-fold upon stimulation of the PMN with the same agonists that induce expression.

Figure 2:
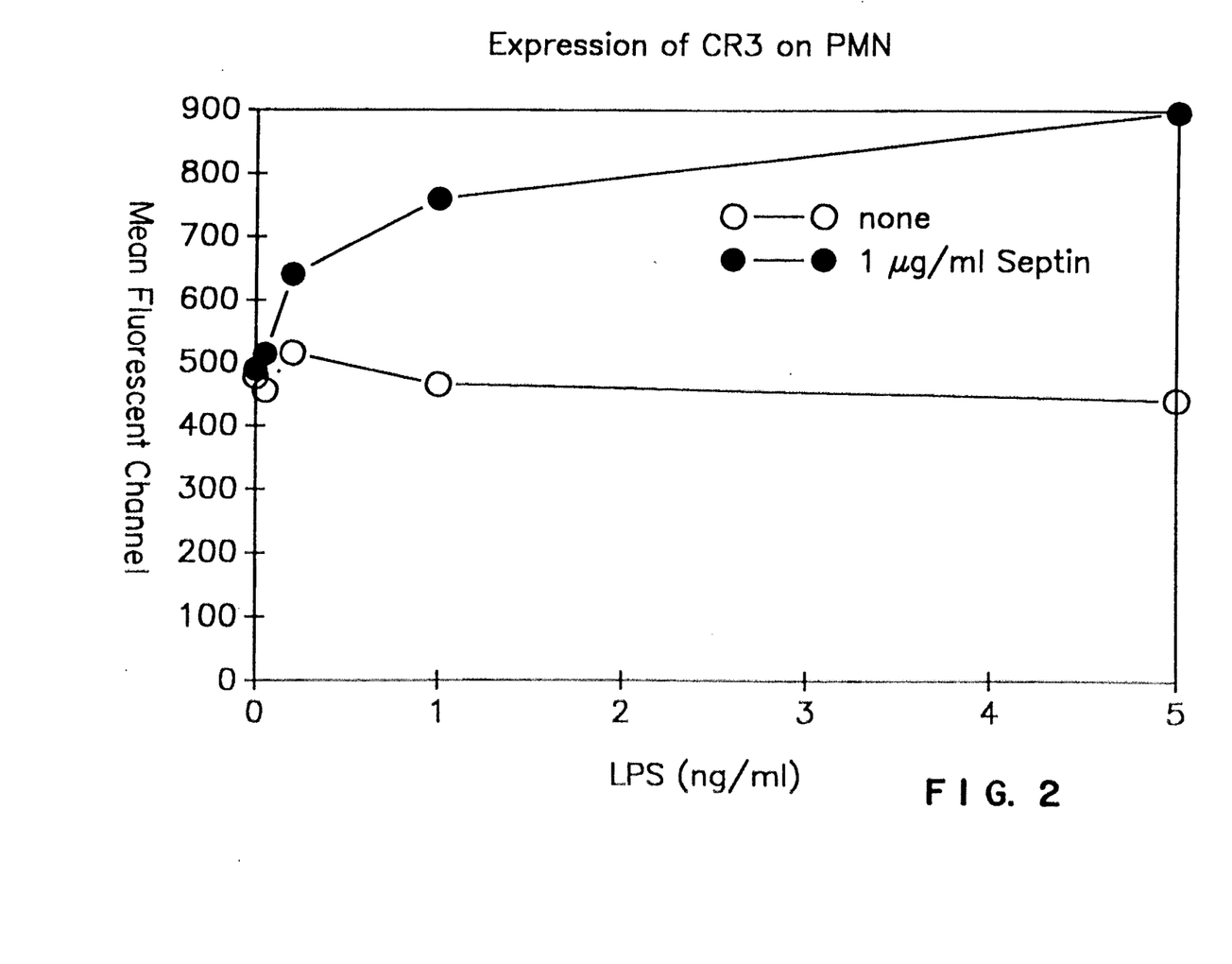

Complexes of septin and LPS cause dramatic stimulation of PMN. Expression of CR3 (CD11b/CD18), an important adhesion molecule, is upregulated two-fold upon exposure of PMN to 1 ng/ml LPS-septin complexes, but neither septin (1 µg/ml) alone nor LPS at concentrations as high as 5 ng/ml cause upregulation (FIG. 2). CR3 resides within secretory granules of PMN, and these data thus suggest that interaction of septin-LPS complexes with CD14 on PMN cause degranulation. The degranulation caused by septin-LPS complexes is clearly not complete however, because parallel studies with the strong agonist, PMA, showed a five-fold increase in expression of CR3 (data not shown).

PMN were admixed with the indicated concentrations of septin and LPS (Re) and added to monolayers of endothelial cells. After 15 minutes at 37° C., the preparations were washed and attachment was measured as described [Lo et al., *J. Exp. Med.*, 169:1779-1793 (1989)], and the results are set forth in Table II, Below. Basal adhesion values for unstimulated cells were subtracted from the data shown.

TABLE II

| Binding of PMN to Umbilical Vein Endothelium | | |
|---|---|---|
| LPS (ng/ml) | −Septin | +Septin (1 µ/ml) |
| 0 | 0 | 115 |
| 0.05 | 135 | 339 |
| 0.20 | 132 | 330 |

Figure 3:
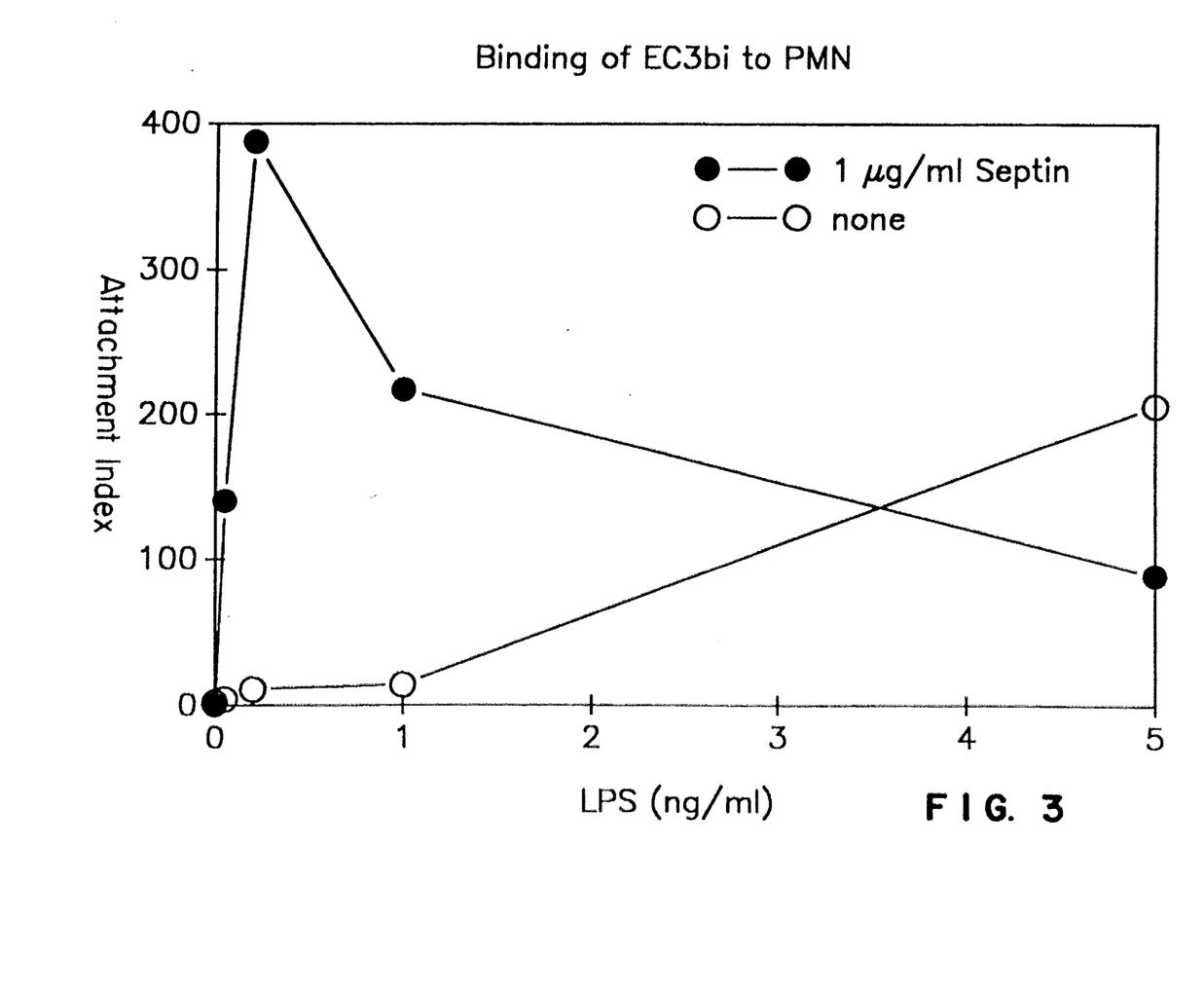

An early event in the response of animals to endotoxin is adhesion of PMN to the endothelium. This adhesive capacity is also stimulated by septin-LPS complexes but not by septin or LPS alone (Table II). CR3 is a dominant receptor that mediates adhesion of stimulated PMN to unstimulated endothelium and incubation of PMN with septin-LPS complexes, but not septin or LPS assayed by ability of CR3 to mediate binding of C3bi-coated erythrocytes (FIG. 3). Other stimuli of PMN such as PMA or IL-8 cause similar increases in CR3 activity, and previous work indicates increased receptor activity is caused both by changes in the number of CR3 on the surface and by changes in the binding activity of existing CR3. Further preliminary studies indicate that concentrations of septin-LPS complexes that cause a strong adhesion response do not stimulate the release of hydrogen peroxide ([J. Cell. Biol., 109:1341 (1980)], not shown).

EXAMPLE 4

Loss of CD14 from the Surface of Stimulated Macrophages

In the course of studies on the response of macrophages to LPS, it was discovered that addition of LPS to macrophages in the presence of 10% human serum caused a dramatic loss of CD14 from the macrophage cell surface. Additional preliminary studies indicate that loss is complete by 3 hours and is caused by doses of LPS as low as 0.1 ng/ml. The following describes experiments that were performed and contributed to this finding.

Accordingly, the stimuli listed in Table III were added to four-day cultures of human monocytes ($10^6$ cells/ml in RPMI 1640 containing 10% normal serum) in Teflon beakers. After an additional 18 hours of culture, cells were washed, stained with monoclonal antibodies and fluoresceinated F(ab)$_2$, and analyzed by FACS. The results are likewise presented in the below Table, with data presented as mean fluorescent intensity (linear scale).

TABLE III

| Loss of CD14 from Macrophages during Response to LPS | | | |
|---|---|---|---|
| | | Stimulant | |
| Antigen | None | LPS (100 ng/ml) | TNFα($10^{-9}$ M) |
| CD14 | 579 | 26 | 1138 |
| CD18 | 1700 | 1636 | 1788 |
| HLA | 2292 | 2472 | 2399 |
| —(ctrl) | 23 | 20 | 24 |

Discussion

As illustrated by the above data, these studies suggest that the signalling of cellular responses by LPS is associated with loss of CD14. Loss of surface CD14 does appear to require signalling by LPS since biologically inactive LPS analogs do not cause loss. It is unlikely that the loss is caused by an autocrine loop involving TNF since TNFe caused an increase, not a decrease, in expression of CD14 (Table III).

The biosynthetic precursor of LPS termed Lipid IVa binds strongly to LBP and septin (not shown). Complexes of LBP and Lipid IVa also appear to bind normally to CD14 since the dose of lipid IVa/erythrocyte needed for half-maximal LBP-dependent binding to MO is the same as the dose of Re endotoxin (not shown). By contrast, complexes of Lipid IVa and the opsonin septin do not bind to CD14, distinguishing the present opsonin from LBP and suggesting that Lipid IVa may function as an inhibitor of septin activity.

Also, Lipid IVa does not trigger TNF synthesis, and recent studies show that addition of lipid IVa strongly antagonizes TNF synthesis in response to Re endotoxin. It was observed that lipid Ira does not cause loss of surface CD14, and in some experiments, it caused an increase (perhaps by antagonizing the effect of contaminating LPS).

EXAMPLE 5

Anti-septin Blocks the Ability of Plasma to Support Binding of ELPS to CD14

Purified septin was mixed with alumagel and injected (4x) into a rabbit. The IgG from preimmune and immune serum was purified and mixed with whole human plasma. While pre-immune IgG had no effect on the binding of ELPS to MO, anti-septin completely blocked binding (Table IV). This experiment indicates that we have developed a blocking antibody and that septin is the protein in plasma with the greatest contribution to the interaction of LPS with macrophages.

TABLE IV

| Anti-septin Blocks Septin Activity | |
|---|---|
| Antibody | Attachment Index (ELPS) |
| None | 419 |
| Preimmune (150 µg/ml) | 488 |
| Anti-septin (150 µg/ml) | 24 |

Antibody was added to plasma and held for 60 min. on ice. Samples were then diluted 1:100 and mixed with macrophages and ELPS. Attachment of erythrocytes to macrophages was then measured.

EXAMPLE 6

Structural Analysis of Septin

Septin was blotted from an SDS gel onto immobilon, and a partial amino acid sequence was obtained. This partial sequence shows no similarity to the functionality related proteins LBP, BPI or CETP, thus confirming the novel nature of septin. However, the partial sequence is similar to a residue of human protein C inhibitor (PCI), a plasma protein of the serpin (serine protease inhibitor) family. This similarity in sequence prompted consideration of the hypothesis that septin is identical with PCI.

Purified PCI and two monoclonal anti-PCI antibodies were provided by Dr. Johan Stenflow (Sweden). Purified PCI had none of the biological activities of septin when assayed over a wide range of concentrations, and monoclonal anti-PCI antibodies failed to either neutralize septin or react in western blots of septin. It is thus believed that septin is structurally related to but distinct from PCI, and may represent a new member of the serpin family.

There is precedent for members of the serpin family serving as binding proteins. Thyroxine binding globulin and corticosteroid binding globulin are both human plasma transport proteins that belong to the serpin family, and it is thus reasonable to hypothesize that a serpin could bind LPS. Similarity of septin to the serpin, PCI, also offers an intriguing potential link to an unexplained phenomenon in sepsis. Infusion of Activated Protein C (APC), an inhibitor of coagulation, prevents death from endotoxic shock by preventing the synthesis of TNF (F. Taylor, personal communication). If septin's similarity to PCI allows it to serve as an inhibitor of APC, then infusion of APC may consume septin and prevent responses to endotoxin.

The typical molecular weight of a serpin (50 kDa) is significantly different from that of septin (90 kDa).

However, it is known that serpins form covalent complexes with their target proteases, and these complexes run on SDS gels as the sum of the molecular weights of the serpin and protease. The acyl intermediate can be disrupted by incubation of the serpin-protease complex with base. We have observed that incubation of septin with 1M ammonium hydroxide results in a shift in molecular weight, giving rise to a 55 kDa and a 34 kDa species. These are most compatible with a model in which septin is actually a complex between a serpin related to PCI, and a protease of 34 kDa.

EXAMPLE 7

Protease Inhibitors Block Septin Activity in Plasma

The finding that septin is apparently composed of a protease and substrate prompted the testing of protease inhibitors. Addition of a mixture of protease inhibitors profoundly reduced the capacity of plasma to support interaction of ELPS with MO (Table V). Additional studies indicate that protease inhibitors blocked interaction of septin with ELPS (Table V), protocol II), not binding of septin-LPS complexes to CD14.

The two most effective protease inhibitors found to date are aprotinin and chymostatin. Since chymostatin preferentially inhibits chymotryptic-like proteases which cleave after hydrophobic residues and aprotinin preferentially inhibits enzymes with trypsin-like enzymes which cleave after basic residues, our results suggest that inhibition of either of two proteases is sufficient to halt the production of septin.

Further studies indicate that the nontoxic protease inhibitor, aprotinin, also interrupts the stimulation of PMN by LPS and septin (Table VI). These data suggest that a proteolytic event, perhaps the interaction of a protease with a serpin, is necessary to generate septin.

TABLE V

Inhibition of Septin Activity by Protease Inhibitors

| Inhibitors | | Decrease in Septin Activity (fold) |
|---|---|---|
| PROTOCOL I[1] | | |
| Antipain, 5 μg/ml | | |
| Leupeptin, 5 μg/ml | experiment 1 | 12 |
| Benzamidine, 25 μg/ml | experiment 2 | 8.5 |
| Chymostatin, 5 μg/ml | experiment 3 | 15 |
| Pepstatin A, 5 μg/ml | | |
| Chymostatin 5 μg/ml + Pepstatin 5 μg/ml | | 5.6 |
| Chymostatin 100 μg/ml | | 18 |
| Aprotinin 100 μg/ml | | 94 |
| PROTOCOL II[2] | | |
| Antipain + Leupeptin + Benzamide | | 3.0 |
| Chymostatin + Pepstatin A | | 3.3 |
| All together | | 10.3 |

[1]In Protocol I, plasma was diluted 100-fold with the indicated concentration of inhibitors and mixed with ELPS and macrophages. The attachment of ELPS to macrophages was determined after a 30 min. incubation, and the decrease in attachment caused by protease inhibitors was determined.
[2]In Protocol II, plasma was diluted 100-fold with the indicated concentration of inhibitors and mixed with ELPS. Following a 20 min. incubation, the ELPS were washed and incubated with macrophages. Attachment was determined as described above.

TABLE VI

Aprotinin Blocks the Serum-dependent Stimulation of PMN by LPS

| Stimulus | | | Attachment Index |
|---|---|---|---|
| LPS (1 ng/ml) | Serum (1:100) | Aprotinin | (EC3bi) |
| − | − | − | 18 |
| + | − | − | 47 |
| − | + | − | 9 |
| + | + | − | 480 |

TABLE VI-continued

Aprotinin Blocks the Serum-dependent Stimulation of PMN by LPS

| Stimulus | | | Attachment Index |
|---|---|---|---|
| LPS (1 ng/ml) | Serum (1:100) | Aprotinin | (EC3bi) |
| + | + | 50 ug/ml | 118 |

PMN were incubated with the indicated dilutions of human serum and LPS in the presence or absence of aprotinin for 30 mins. at 37° C. The cells were then washed and activation of CR3 was assayed by measuring the binding of C3bi-coated sheep erythrocytes (EC3bi).

Further evidence that a complex between protease and inhibitor is required to form septin derives from experiments in which several fractions from a Mono Q column were combined. While the septin peak contains an amount of activity equal to 0.2-1% of the septin activity applied, a pool of all peaks contains 50-80% of the activity loaded. Thus, a mixture of proteins, presumably protease and substrate, must be combined to form septin. We believe that the activity present in the "septin" peak represents a small amount of pre-formed protease-serpin complex.

Other proteins in plasma function in a protease cascade to initiate biological effects. For example, the complement cascade is initiated by very small amounts of immune complex, and the contact system of the clotting cascade is initiated by anionic surfaces. Septin appears to be the product of a similar cascade. To rule out the possibility that proteins from known protease cascades participate in the "septin cascade," we measured the septin activity in plasma depleted of particular proteins. Serum deficient in complement protein C5, and complement proteins C2 and Factor B (heated serum) had normal septin levels. Septin levels were not affected by clotting of plasma. Further, plasma deficient in Protein C, Hageman Factor, prekallikrein, High molecular weight kininogen, or Factor IX showed normal septin levels. Thus, the enzymatic reactions described here represent a novel protease cascade and this cascade is an object of the current invention.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. An antibody which specifically binds a protein, septin, wherein septin is an opsonin possessing an apparent molecular weight of about 90 kD as determined by SDS-PAGE analycio, and septin is capable of binding to lipopolysaccharide to form a complex that is recognized by a receptor on monocytes, macrophage cells and polymorphonuclear cells.

2. The antibody of claim 1 as raised in rabbits and developed to an immunoglobulin (IgG) from immune serum.

3. The antibody of claim 1 comprising a polyclonal antibody.

4. The antibody of claim 1 comprising a monoclonal antibody.

5. An immortal cell line that produces a monoclonal antibody according to claim 4.

6. The antibody of claim 1 labeled with a detectable label.

7. The antibody of claim 6 wherein the label is selected from the group consisting of enzymes, chemicals which fluoresce, and radioactive elements.

* * * * *